1227133B2

United States Patent
Hsu et al.

(10) Patent No.: US 11,227,133 B2
(45) Date of Patent: Jan. 18, 2022

(54) PRODUCT LABEL, SYSTEM AND METHOD FOR PROVIDING INSTANT INFORMATION OF FRESH FOOD

(71) Applicant: TAIWAN CARBON NANO TECHNOLOGY CORPORATION, Miaoli County (TW)

(72) Inventors: Ching-Tung Hsu, Miaoli County (TW); Chao-Chieh Lin, Miaoli County (TW); Yuan-Shin Huang, Miaoli County (TW); Chun-Wei Shih, Miaoli County (TW); Chia-Hung Li, Miaoli County (TW); Chun-Hsien Tsai, Miaoli County (TW); Chun-Jung Tsai, Miaoli County (TW)

(73) Assignee: TAIWAN CARBON NANO TECHNOLOGY CORPORATION, Zhuan Township, Miaoli County (TW)

( * ) Notice: Subject to any disclaimer, the term of this patent is extended or adjusted under 35 U.S.C. 154(b) by 0 days.

(21) Appl. No.: 17/097,859

(22) Filed: Nov. 13, 2020

(65) Prior Publication Data
US 2021/0150168 A1    May 20, 2021

(30) Foreign Application Priority Data

Nov. 15, 2019   (TW) ................................ 108141585

(51) Int. Cl.
| | |
|---|---|
| *G06K 7/10* | (2006.01) |
| *G06K 7/14* | (2006.01) |
| *G01N 33/02* | (2006.01) |
| *G01N 21/78* | (2006.01) |

(52) U.S. Cl.
CPC .......... *G06K 7/1417* (2013.01); *G01N 21/78* (2013.01); *G01N 33/025* (2013.01); *G06K 7/10554* (2013.01)

(58) Field of Classification Search
CPC .. G01N 33/025; G01N 21/78; G06K 7/10554; G06K 7/1417
See application file for complete search history.

(56) References Cited

U.S. PATENT DOCUMENTS

| | | | |
|---|---|---|---|
| 2002/0173040 A1* | 11/2002 | Potyrailo | G01N 33/28 436/2 |
| 2011/0050431 A1* | 3/2011 | Hood | G01N 33/14 340/603 |
| 2015/0064703 A1* | 3/2015 | Super | G01N 33/56911 435/6.12 |

(Continued)

*Primary Examiner* — Thien M Le
(74) *Attorney, Agent, or Firm* — Muncy, Geissler, Olds and Lowe, P.C.

(57) ABSTRACT

The present invention provides a product label with a colorimetric sensor array and a code, and the system and the method of the present invention are mainly that the product label is attached to a fresh food, so that at least one sensing material of the colorimetric sensor array undergoes a chemical reaction with at least one metabolic molecule of the fresh food to change from an initial color to an indicating color. The present invention, by obtaining an image comprising an appearance, the code and the indicating color of the fresh food through an image acquisition device, also provides an instant information associated with the fresh food by a processing device according to a comparison result of the image and a database.

9 Claims, 8 Drawing Sheets

(56) References Cited

U.S. PATENT DOCUMENTS

| | | | | |
|---|---|---|---|---|
| 2018/0180554 | A1* | 6/2018 | Huang | G01N 33/0031 |
| 2018/0282780 | A1* | 10/2018 | Singh | C12Q 1/18 |
| 2020/0062456 | A1* | 2/2020 | Granevitze | C12Q 1/04 |
| 2020/0300774 | A1* | 9/2020 | Hsu | G01N 33/02 |
| 2020/0302379 | A1* | 9/2020 | Hsu | G06Q 10/087 |

* cited by examiner

PRODUCT LABEL, SYSTEM AND METHOD FOR PROVIDING INSTANT INFORMATION OF FRESH FOOD

FIELD OF THE INVENTION

The invention relates to a product label, in particular to a product label, a system and a method capable of providing instant information of fresh food.

BACKGROUND OF THE INVENTION

In order to improve the edible safety of the fresh food, attaching a product label on the fresh food is a common practice, and through a common product label such as a plu code, a planting method, a fruit producing area, size specifications and the like can be known. The product label as described above can only disclose conventional and limited information, and obviously cannot provide the consumer with instant information of the fresh food.

"System and method for controlling time limit of commodity by scanning two-dimensional bar code connected to cloud server" is disclosed in ROC invention patent number 1625685, which discloses a system and method for controlling a time limit of a commodity in order to convert a commodity code and commodity information into a two-dimensional bar code and print the two-dimensional bar code on a card, and the two-dimensional bar code can be obtained and photographed by a consumer along with the sale of the commodity to connect to a database for obtaining a corresponding commodity code and commodity data, such as attentions, a preservation mode, an expiration date, a manufacturing date and the like. When the patent is applied to fresh foods, consumers can fully master the production information of the fresh foods and know the best preservation mode, the best expiration date and the like.

However, the instant information of the fresh food is greatly associated with the preservation mode, and the instant information of the fresh food having the same production information is greatly different under different preservation modes. For example, in a low temperature environment, fruits may be stored for a relatively long period of time, while at normal temperatures, there is often a shelf life of only a few days, so that consumers can only make judgment empirically from changes in appearance, smell, and hardness, and general consumers often have a wrong judgment.

SUMMARY OF THE INVENTION

The invention mainly aims to disclose a system and a method for providing instant information of fresh foods, so that consumers can know the instant information of the fresh foods to serve as references for purchasing.

In order to achieve the object, the invention discloses a product label, which is used for attaching to a fresh food and includes a film and a colorimetric sensor array. The film is attached to the fresh food. The colorimetric sensor array is formed on the film, the colorimetric sensor array includes at least one sensing material, and the at least one sensing material is used for sensing the fresh food, wherein the at least one sensing material undergoes a chemical reaction with at least one metabolic molecule of the fresh food to change from an initial color to an indicating color.

The system of the present invention includes a product label, an image acquisition device and a processing device. The product label further includes a code, and the code is displayed on the film and is associated with the fresh food. The image acquisition device acquiring an image including an appearance, the code and the indicating color of the fresh food. The processing device provides an instant information associated with the fresh food according to a comparison result of the image and a database.

The method of the present invention is used for enabling a consumer to know an instant information of a fresh food, and includes the following steps of
 attaching the product label to the fresh food;
 establishing the database, wherein the database stores at least one information of the fresh food;
 obtaining the image by using the image acquisition device for the consumer; and
 providing the instant information associated with the fresh food according to a comparison result of the image and the database by a processing device.

Accordingly, a consumer can obtain the indicating color of the colorimetric sensor array and the appearance of the fresh food through the image acquisition device, such that the consumer can know the instant information of the fresh food through the processing device, the instant information includes instant flavor information of the fresh food, such as maturity, fragrance concentration, sweetness and the like, and the consumer can judge whether to purchase the fresh product in a non-contact manner.

DETAILED DESCRIPTION OF THE PREFERRED EMBODIMENTS

Figure 1A:
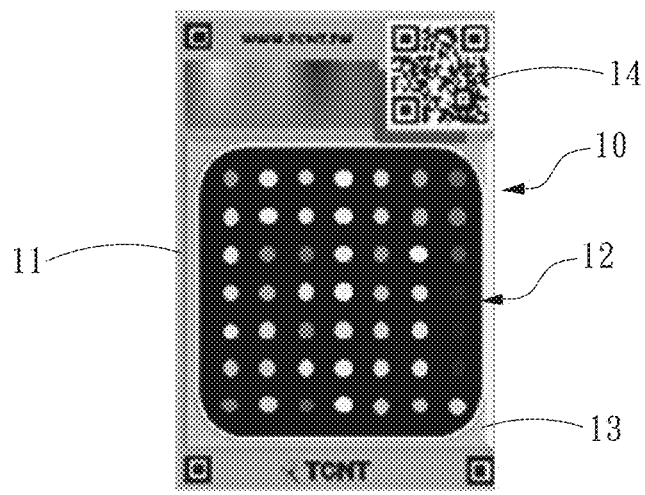
FIG. 1A is a schematic diagram showing an appearance of a product label of the present disclosure.
Figure 1B:
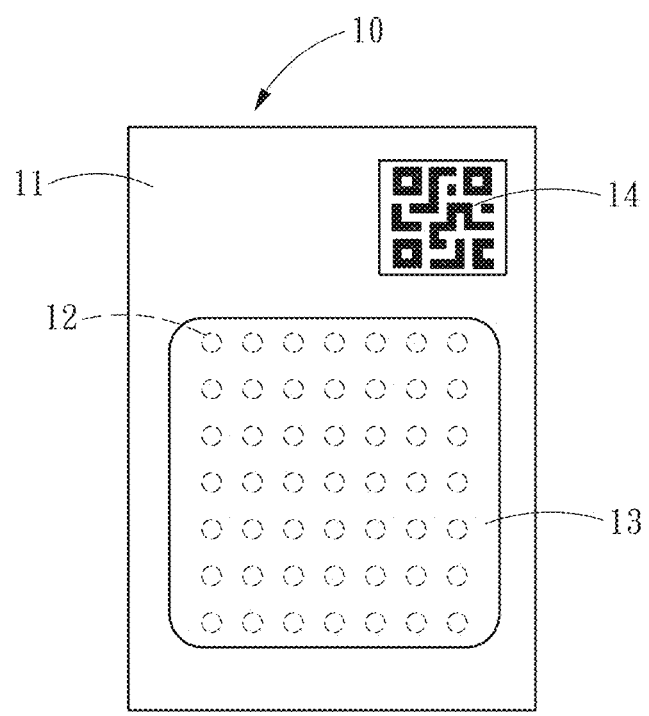
FIG. 1B is a schematic diagram showing the appearance of the product label of the present disclosure.
Figure 2:
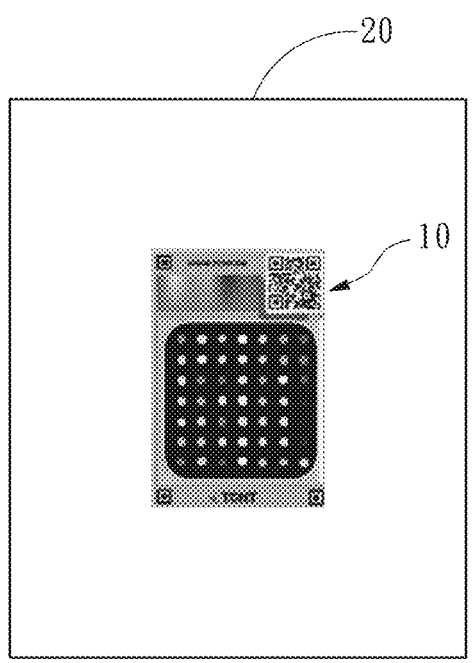
FIG. 2 is a schematic diagram showing the use of the product label of the present disclosure.

With respect to the detailed description and technical aspects of the present disclosure, reference is now made to the following descriptions taken in conjunction with the accompanying drawings:

With reference to FIG. 1A, FIG. 1B and FIG. 2, the present invention discloses a product label 10 for attaching to a fresh food 20. The product label 10 includes a film 11 and a colorimetric sensor array 12, wherein the film 11 is attached to the fresh food 20 and the colorimetric sensor array 12 is formed on the film 11. The colorimetric sensor array 12 includes at least one sensing material which is used for sensing the fresh food 20. The at least one sensing material undergoes a chemical reaction with at least one metabolic molecule of the fresh food 20 to change from an initial color to an indicating color. In one embodiment, a plurality of sensing material is provided and are formed on the film 11 in a pixel-like such as 7*7 sensing pixels.

The at least one sensing material is selected according to the design function of the colorimetric sensor array 12, and the at least one sensing material includes a coloring reagent selected from a group consisting of methyl red, Congo red, bromophenol blue, bromocresol purple, bromocresol green, cresol red, phenol red, thymolphthalein, resazurin, paranitrophenol, hromthymol blue, thymol blue, neutral red, crystal violet, 4-(4-nitrobenzyl) pyridine, pyrocatechol violet, chlorophenol red, nitrazine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow K, indigo carmine, rile blue A, orange yellow G, Eosin B, 3,3',5,5', -tetraiodophenol sulfone phenolphthalein, bromoxylenol blue, phenol blue, disperse orange 25, acridine orange, disperse orange 3, disperse red 1, bromoopyrogallol red, diaminodiphenyl acer, aminofluorescein, violet ammonium urea, 6-dichloroindophenol, catechil violet, sodium salts thereof, and mixtures thereof.

In one embodiment, the at least one sensing material further includes a molecular barrier material selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers (CNF), silicone compounds, and the like. The molecular barrier material can be mixed with the coloring reagent to form the sensing pixel, and the molecular barrier material can also be coated on the coloring reagent to form the sensing pixel. The molecular barrier material can influence a reaction speed of the at least one sensing material, such that the reaction speed can be modified and controlled by selecting different molecular barrier materials to meet the use requirement.

In order to prevent damage from external forces or ultraviolet rays, the product label 10 further includes a protective layer 13 covering the colorimetric sensor array 12, blocking ultraviolet rays, and shielding the colorimetric sensor array 12 to prevent the colorimetric sensor array 12 from failing or being damaged by external forces. A code 14 may be displayed on the film 11 to be associated with the fresh food 20, the code 14 is determined according to at least one information of the fresh food 20, the at least one information is selected from a group consisting of a history information, a quality information, and an initial appearance. The code 14 can be a string of numbers, or a one-dimensional bar code, or a two-dimensional bar code (QR code), etc.

Figure 3:
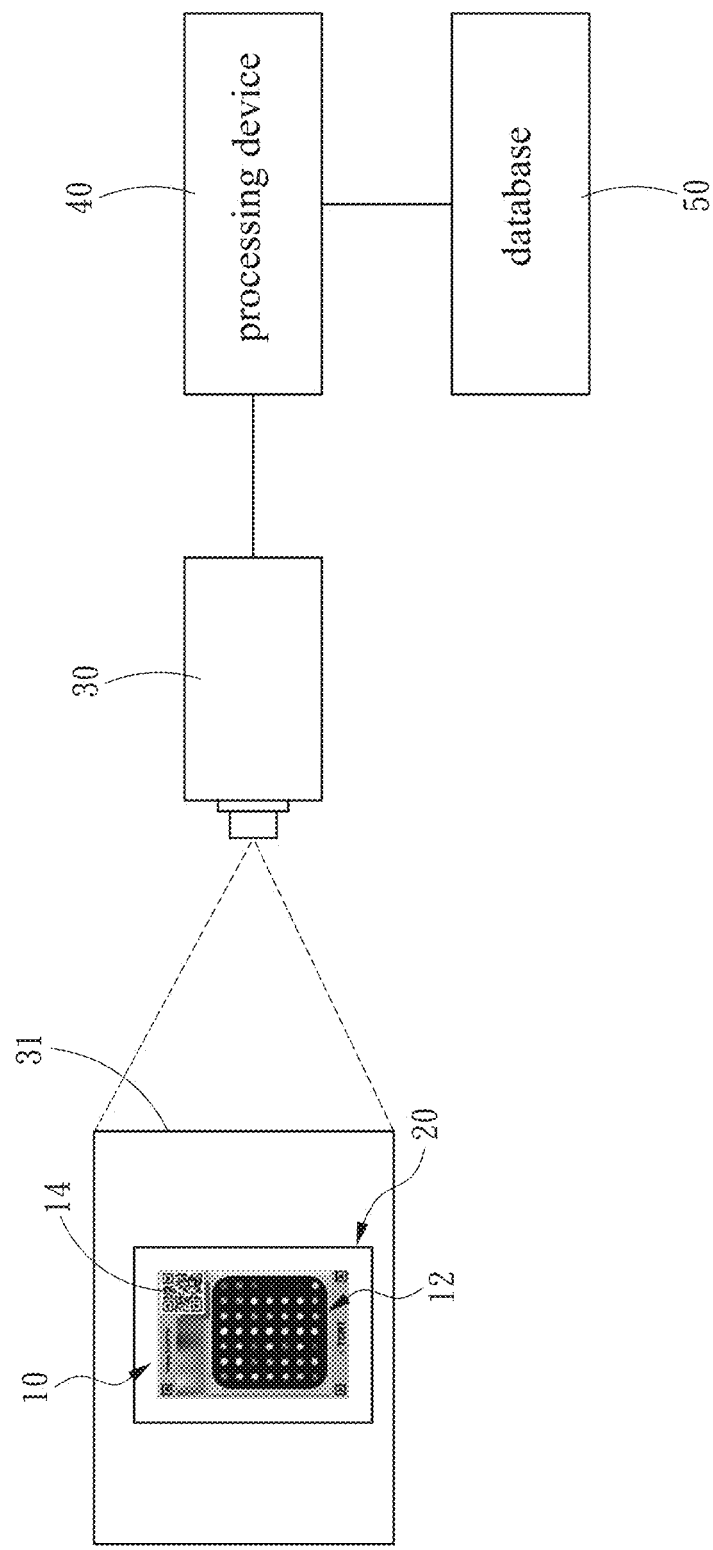
FIG. 3 is a schematic diagram of the system architecture of the present disclosure.

With reference to FIG. 3, the system of the present invention includes the product label 10, an image acquisition device 30 and a processing device 40. The image acquisition device 30 acquires an image 31 including an appearance of the fresh food 20, the code 14 and the indicating color of the colorimetric sensor array 12. The processing device 40 provides an instant information associated with the fresh food 20 according to a comparison result of the image 31 and a database 50.

Figure 4:
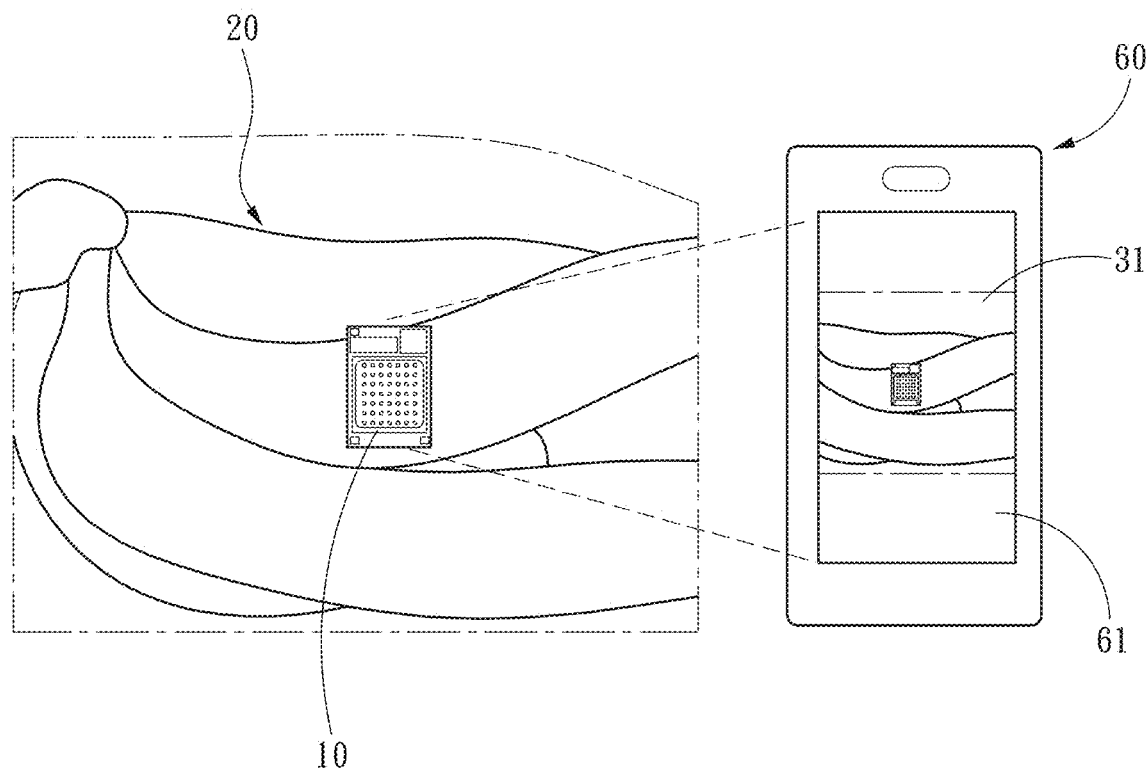
FIG. 4 is a schematic diagram for obtaining an image according to the present disclosure.
Figure 5:
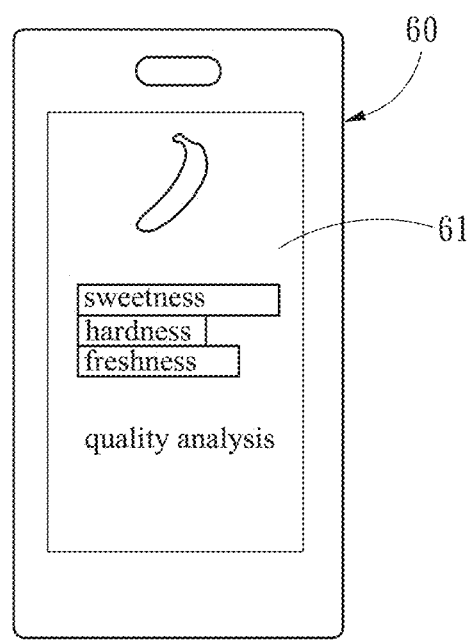
FIG. 5 is a schematic diagram for providing an instant information according to the present disclosure.

With reference to FIG. 3, FIG. 4 and FIG. 5, the method of the present invention is provided for a consumer to know the instant information of the fresh food 20 (using a banana as an illustration) includes the steps of:

attaching the product label 10 to the fresh food 20;

establishing the database 50, wherein the database 50 stores the information of the fresh food 20;

acquiring the image 31 by using the image acquisition device 30 for the consumer; and providing the instant information associated with the fresh food 20 according to the comparison result of the image 31 and the database 50 through the processing device 40.

The image acquisition device 30 and the processing device 40 may be elements in a portable intelligent device 60 such as an intelligent mobile phone (e.g., FIG. 4), a tablet computer, etc., and the instant information of the fresh food 20 may also be displayed on a screen 61 of the portable intelligent device 60 (e.g., FIG. 5), order to facilitate the consumer to read the instant information of the fresh food 20, which includes sweetness, hardness, freshness, etc.

Figure 6A:
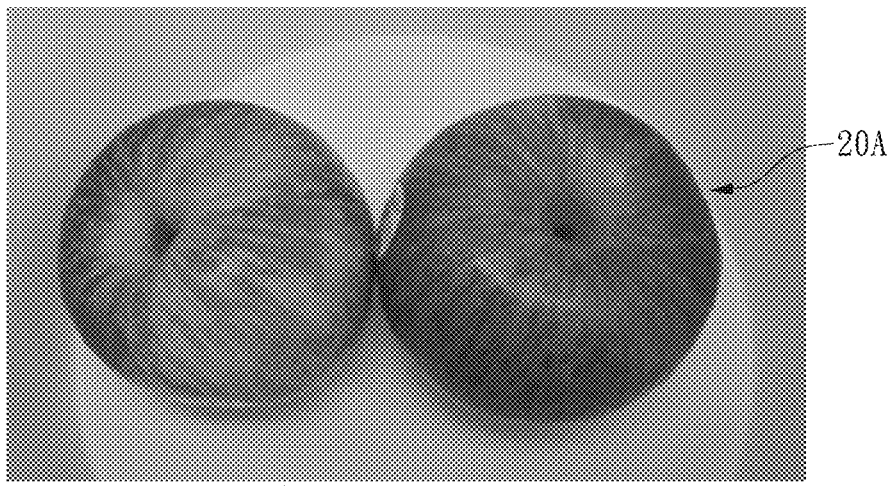
FIG. 6A is a schematic photograph of fresh apples in a first embodiment of the present disclosure.
Figure 6B:
FIG. 6B is a schematic photograph of non-fresh apples in the first embodiment of the present disclosure.
Figure 6C:
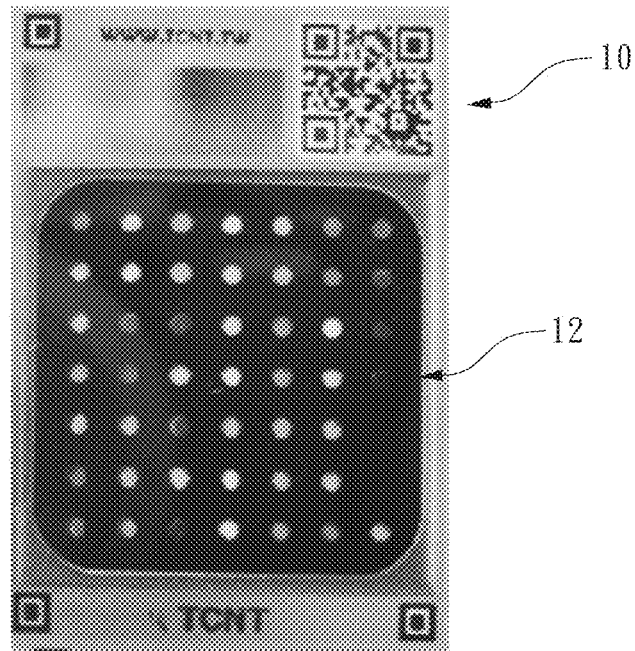
FIG. 6C is a photograph showing an initial color of the first embodiment of the present disclosure.
Figure 6D:
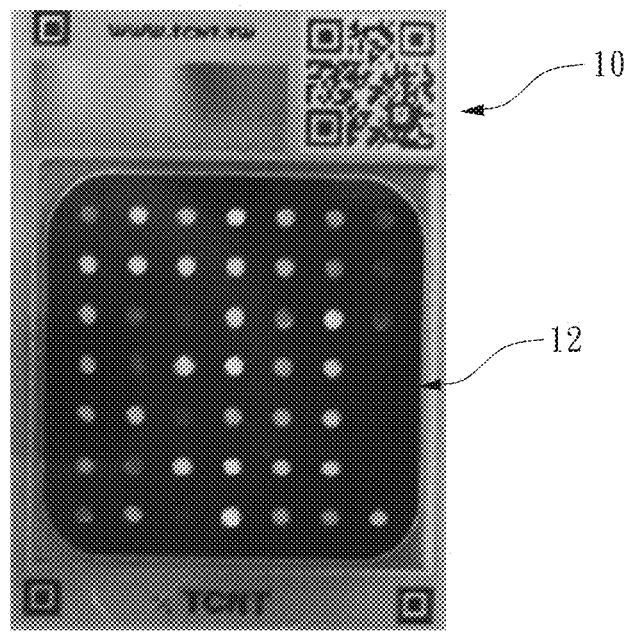
FIG. 6D is a photograph showing an indicating color of the first embodiment of the present disclosure.

With reference to FIG. 3, FIG. 6A, FIG. 6B, FIG. 6C, and FIG. 6D, in accordance with a first embodiment of the present invention, fresh food 20A is taking apple as an example for illustration, FIG. 6A is a schematic photograph of fresh apples, and FIG. 6B is a schematic photograph of non-fresh apples. Most apples on the market are sprayed with wax to simulate a fresh appearance for increasing selling, which results in a little difference in appearance between FIG. 6A and FIG. 6B. However, the apples of FIG. 6B are actually not fresh any more, which may cause poor taste and hygienic problems. By comparing the color of the colorimetric sensor array 12 of the product label 10 in FIG. 6C with the indicating color of the colorimetric sensor array 12 of the product label 10 in FIG. 6D, the significant change of the indicating color can be known. Therefore, by obtaining the image 31 through the image acquisition device 30, the processing device 40 can provide instant information of the fresh food 20A (apple) according to the comparison result of the image 31 and the database 50, so that the consumer can learn that the apple has deteriorated.

Figure 7A:
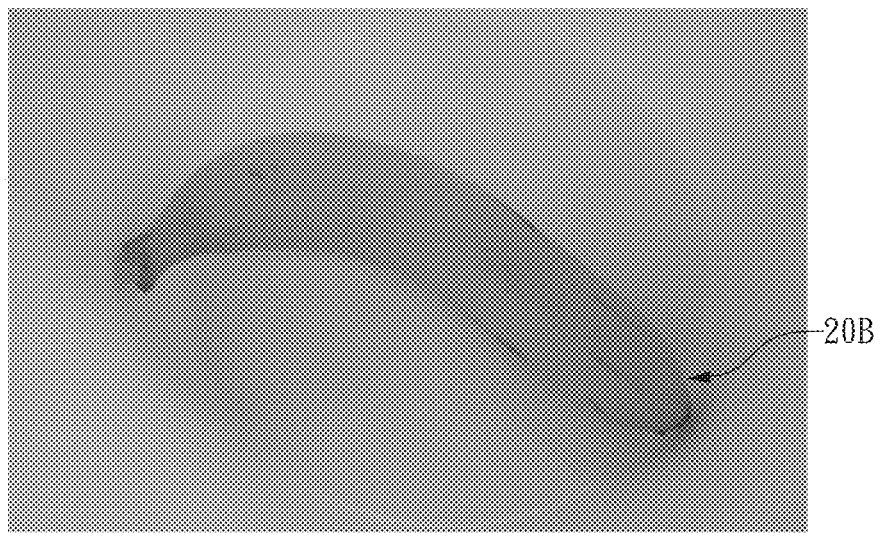
FIG. 7A is a schematic photograph of a fresh banana in a second embodiment of the present disclosure.
Figure 7B:
FIG. 7B is a schematic photograph of a non-fresh banana in the second embodiment of the present disclosure.
Figure 7C:
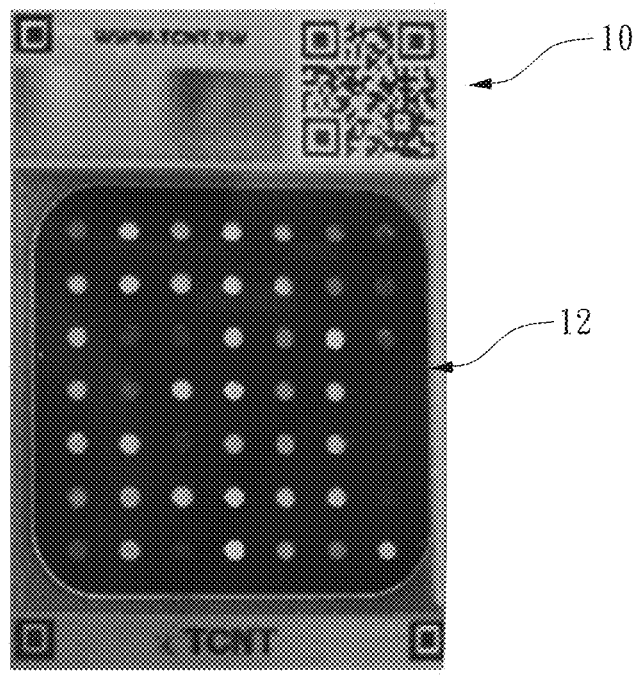
FIG. 7C is a photograph showing the initial color of the second embodiment of the present disclosure.
Figure 7D:
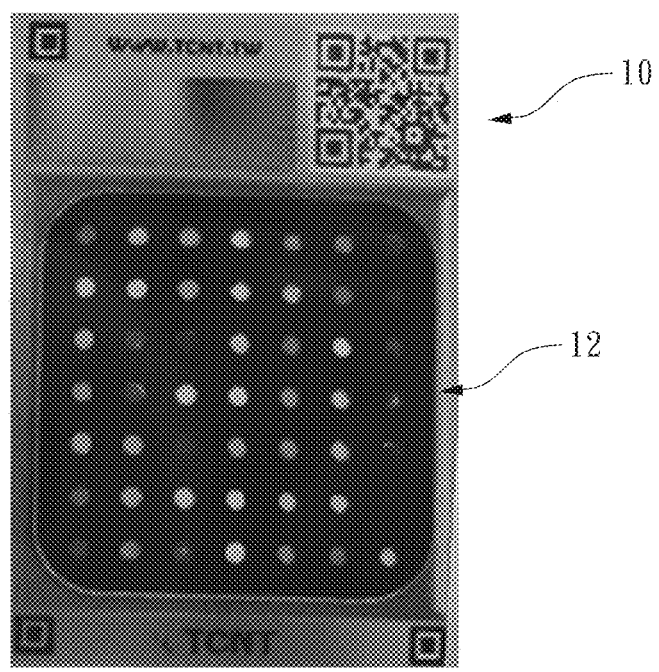
FIG. 7D is a photograph showing the indicating color of the second embodiment of the present disclosure.

With reference to FIG. 3, FIG. 7A, FIG. 7B, FIG. 7C, and FIG. 7D, in accordance with the second embodiment of the present invention, the fresh food 20B is illustrated as banana. FIG. 7A is a schematic photograph of a fresh banana, and FIG. 7B is a schematic photograph of a non-fresh banana. The banana must be waited for ripening to have good taste and flavor before consuming, and usually needs to be placed at room temperature for 2 days to 3 days, but a ripening speed of the banana is fast, and a problem of rotting will be occurred once the banana is placed for too long. Taking an example of the appearance of the banana as shown in FIG. 7A and FIG. 7B, which has significantly changed. However, it cannot be judged whether the banana has rotted, By comparing the initial color of the colorimetric sensor array 12 of the product label 10 in FIG. 7C with the indicating color of the colorimetric sensor array 12 of the product label 10 in FIG. 7D to determine whether the banana have spoiled, i.e., the consumer obtains the image 31 by using the image acquisition device 30 only and the processing device 40 can provide instant information on whether the fresh food 20B (banana) has rotted according to the comparison result of the image 31 and the database 50.

According to the invention, the characteristics of the present invention at least include:

1. The consumer obtains the indicating color of the colorimetric sensor array and the appearance of the fresh food by using the image acquisition device, so that the consumer can know the instant information of the fresh food, such as maturity, fragrance concentration, sweetness and the like, through the processing device. The consumer can judge the condition of the fresh food, and the provider can popularize the fresh food to the consumer by using the instant information.

2. The instant information of the fresh food can be obtained only by photographing, which is a non-contact mode, and fruits can be prevented from being damaged.

What is claimed is:

1. A product label for attaching to a fresh food comprising:
   a film attached to the fresh food; and
   a colorimetric sensor array formed on the film, the colorimetric sensor array comprising at least one sensing material for sensing the fresh food and a molecular barrier material for influencing a reaction speed of the at least one sensing material, wherein the at least one sensing material undergoes a chemical reaction with at least one metabolic molecule of the fresh food to change from an initial color to an indicating color.

2. The product label according to claim 1, further comprising a protective layer covering the colorimetric sensor array.

3. The product label according to claim 1, wherein a code associated with the fresh food is displayed on the film, the code is determined according to at least one information of the fresh food, and the at least one information is selected from a group consisting of history information, quality information, and an initial appearance.

4. A system for providing instant information of a fresh food comprising:
   a product label, having a film attached to the fresh food, a code displayed on the film and associated with the fresh food, and a colorimetric sensor array formed on the film, the colorimetric sensor array comprising at least one sensing material for sensing the fresh food and a molecular barrier material for influencing a reaction speed of the at least one sensing material, the at least one sensing material undergoing a chemical reaction with at least a metabolic molecule of the fresh food undergo a chemical reaction to change from an initial color to an indicating color;
   an image acquisition device, acquiring an image comprising an appearance of the fresh food, the code and the indicating color; and
   a processing device, providing an instant information associated with the fresh food according to a comparison result of the image and a database.

5. The system according to claim 4, further comprising a protective layer covering the colorimetric sensor array.

6. The system according to claim 4, wherein the code is determined according to at least information of the fresh food, and the information is selected from a group consisting of history information, quality information, and an initial appearance.

7. A method for providing instant information of fresh food, which is used for enabling a consumer to know an instant information of a fresh food, comprising the steps of:
   attaching a product label to the fresh food, wherein the product label comprises a film attached to the fresh food, a code displayed on the film and associated with the fresh food, and a colorimetric sensor array formed on the film, the code is determined according to at least one information of the fresh food, the colorimetric sensor array comprises at least one sensing material for sensing the fresh food and a molecular barrier material for influencing a reaction speed of the at least one sensing material, and the sensing material undergoes a chemical reaction with at least one metabolic, molecule of the fresh food to change from an initial color to an indicating color;
   establishing a database, wherein the database stores the at least one information of the fresh food;
   obtaining an image comprising an appearance of the fresh food, the code and the indicating color by using an image acquisition device for the consumer; and
   providing the instant information associated with the fresh food according to a comparison result of the image and the database by a processing device.

8. The method according to claim 7, wherein the at least one information is selected from a group consisting of history information, quality information, and an initial appearance.

9. The method according to claim 7, wherein the product label further comprises a protective layer covering the colorimetric sensor array.

* * * * *